(12) United States Patent
Perry

(10) Patent No.: US 8,557,310 B2
(45) Date of Patent: Oct. 15, 2013

(54) COMPOSITION TO RETARD THE ONSET OF SYMPTOMS OF ALZHEIMER'S DISEASE

(76) Inventor: Stephen C. Perry, Norwood, MA (US)

(*) Notice: Subject to any disclaimer, the term of this patent is extended or adjusted under 35 U.S.C. 154(b) by 0 days.

(21) Appl. No.: 13/236,420

(22) Filed: Sep. 19, 2011

(65) Prior Publication Data

US 2012/0009278 A1    Jan. 12, 2012

Related U.S. Application Data

(63) Continuation-in-part of application No. 10/907,714, filed on Apr. 13, 2005, now Pat. No. 8,021,701.

(51) Int. Cl.
*A61K 36/906* (2006.01)
*A61K 36/67* (2006.01)
*A61K 36/00* (2006.01)

(52) U.S. Cl.
USPC ............... 424/756; 424/734; 424/776

(58) Field of Classification Search
None
See application file for complete search history.

(56) References Cited

U.S. PATENT DOCUMENTS

2003/0203057 A1\* 10/2003 Okada et al. ............... 424/750

\* cited by examiner

*Primary Examiner* — Chris R Tate
*Assistant Examiner* — Deborah Davis
(74) *Attorney, Agent, or Firm* — Johnson & Martin, P.A.; James David Johnson

(57) ABSTRACT

Compositions and methods are described for delaying the onset of the symptoms of Alzheimer's disease in humans. The compositions can include curcumin, piperine, oleic acid, oleanolic acid, ursolic acid, galantamine, and huperzine A, among other compounds. Curcumin is an antioxidant, while galantamine and huperzine A inhibit the activity of acetylcholinesterase in the brain. Piperine and oleic acid increase the bioavailability and gastrointestinal absorption of curcumin, galantamine, huperzine A, and other nutrients. The composition can also include at least one of phytic acid, piracetam, aniracetam, or indium.

15 Claims, No Drawings

COMPOSITION TO RETARD THE ONSET OF SYMPTOMS OF ALZHEIMER'S DISEASE

CROSS-REFERENCE TO RELATED APPLICATION

This application claims the priority from U.S. nonprovisional patent application Ser. No. 10/907,714 filed Apr. 13, 2005. The foregoing application is incorporated in its entirety herein by reference.

FIELD OF THE INVENTION

The invention relates to dietary supplements. More particularly, the invention relates to compositions and methods for using said compositions as dietary supplements to increase the transfer of curcumin and other dietary substances and nutrients from the gastrointestinal tract into the bloodstream to retard the onset of symptoms of Alzheimer's disease in humans.

BACKGROUND

Alzheimer's disease is a debilitating degenerative affliction of the nervous system, which will become increasingly common during the next three decades as the American population ages. In the baby-boomer generation in particular, has aged. Current estimates reveal that by 2035, when the average individual of the "baby boomer" generation is age 85, potentially 50% of Americans will have developed Alzheimer's disease. By providing a treatment that can delay the onset of symptoms of Alzheimer's by as little as five years, at age 85, fifty percent of the United States cases of Alzheimer's could be eliminated. Alzheimer's disease has a negative impact on an individual's memory and cognitive functions, ability to perform the simple activities of daily living, and causes behavioral problems among its sufferers with which families must learn to cope. Typically, Alzheimer's disease also reduces the lifespan of an individual by increasing one's risk of succumbing to secondary infections and illnesses. The disease is associated with the accumulation of β-amyloid plaques in the brain which leads to the eventual destruction of brain cells. The primary cause of Alzheimer's disease may be flaws in the metabolic processes governing production, accumulation, or disposal of the β-amyloid protein fragments. Therefore, treatments for Alzheimer's disease often have focused on dissolving β-amyloid or preventing the aggregation of the β-amyloid fragments into plaque formations.

Recent research has shown that people indigenous to the Indian subcontinent exhibit a much lower incidence of Alzheimer's disease than people living in the United States. Moreover, the research indicated that less than one percent of individuals in the examined population on the Indian subcontinent developed Alzheimer's and that the overall incidence rates of the disease in that location are among the lowest ever reported. V. Chandra et al., Incidence of Alzheimer's disease in a rural community in India: the Indo-US study, Neurology, 57(6): 985-989 (2001). Some researchers have attributed the low incidence of Alzheimer's disease in India to regional diets that are high in the curry spice, turmeric. Turmeric contains a substance, curcumin, which has demonstrated metabolic activity similar to non-steroidal anti-inflammatory drugs. Giselle P. Lim et al., The Curry Spice Curcumin Reduces Oxidative Damage and Amyloid Pathology in an Alzheimer Transgenic Mouse, Journal of Neuroscience, 21(21), 8370-8377 (2001).

Curcumin, a phenolic antioxidant phytochemical derived from the turmeric plant (*Curcuma longa*), is an effective antioxidant, antispasmodic, anti-inflammatory, anticoagulant, anticarcinogenic, and aids immunomodulatory activities and wound healing in the body. Id. at 8370. Curcumin exhibits an affinity for β-amyloid and both inhibits the aggregation of β-amyloid fragments into plaque formations as well as dissolves existing β-amyloid plaques. F. Yang et al., Curcumin inhibits formation of Aβ oligomers and fibrils, binds plaques and reduces amyloid in vivo, Journal of Biological Chemistry (2004).

As an antioxidant, curcumin removes harmful free radicals from the body, thereby protecting the human body, and particularly, the brain, by preventing lipid peroxidation. This antioxidant property of curcumin limits the formation and accumulation of β-amyloid plaques within the brain. Giselle P. Lim et al., The Curry Spice Curcumin Reduces Oxidative Damage and Amyloid Pathology in an Alzheimer Transgenic Mouse, Journal of Neuroscience, 21(21), at 8370 (2001). The non-steroidal anti-inflammatory activity of curcumin includes inhibiting cyclooxygenase 2, nuclear factor κB-mediated transcription of inflammatory cytokines, and the inhibition of inducible nitric oxide synthase. Id. at 8372. Research has shown that parenteral administering both low and high doses of curcumin reduces inflammation in the brain. Id. at 8373. Curcumin may also stimulate microglial phagocytosis of amyloid in the brain as well as destroy plaques that accumulate within the brain. Id. at 8375.

One disadvantage to the use of curcumin as an oral dietary supplement is that curcumin is poorly absorbed from inside the gastrointestinal tract into the human bloodstream. When ingested, curcumin normally remains in the gastrointestinal tract and uptake into the bloodstream is negligible. R. A. Sharma, Preclinical pharmacokinetic study of dietary curcumin and its effects on biomarkers of cancer chemoprevention, Clinical Cancer Research, Volume 6 (2000). Even with high dietary intake, curcumin is rapidly glucuronidated after ingestion, thereby resulting in low plasma levels of curcumin. F. Yang et al., Curcumin inhibits formation of Aβ oligomers and fibrils, binds plaques and reduces amyloid in vivo, Journal of Biological Chemistry, p. 22 (2004). Thus, current research indicates that orally administered curcumin, for the most part, is excreted in the feces without being absorbed and processed by the human body. To make available the beneficial effects of curcumin to Alzheimer's sufferers, the bioavailability of curcumin in the human body must be increased. Currently, clinical trials are being conducted at the University of California, Los Angeles, to examine the safety and tolerability of intravenous curcumin, and to determine the effect curcumin has as a treatment for patients suffering from mild to moderate Alzheimer's disease. John Ringman & Jenny Bardens, A Phase II, Double-Blind, Placebo-Controlled Study of the Safety and Tolerability of Two Doses of Curcumin C3 Complex versus Placebo in Patients with Mild to Moderate Alzheimer's Disease, National Institutes of Health, ClinicalTrials.gov (2003).

Piperine, a botanical extract from the fruits of *Piper nigrum* (black pepper) and *Piper longum*, has been determined to increase the bioavailability of curcumin in the body when both curcumin and piperine are taken together. Studies have shown that oral administration of 20.0 mg of piperine with 2.0 grams of curcumin increases the bioavailability of curcumin by 2,000%. U.S. Pat. No. 6,054,585, issued to Majeed et al., on Apr. 25, 2000, describes a process for making high-purity piperine from black pepper or long pepper for nutritional uses, however the '585 patent does not discuss the use of curcumin with piperine as a means for retarding the onset of Alzheimer's disease. U.S. Pat. Nos. 5,536,506, 5,744,161, and 5,972,382, issued to Majeed et al., on Jul. 16, 1996, Apr. 28, 1998, and Oct. 26, 1999, respectively, all describe the use of piperine as a bioavailability enhancer for aiding and improving gastrointestinal absorption and systemic utilization of nutrients and nutritional supplements. The use of piperine to enhance the bioavailability of curcumin and other beneficial substances, which are not easily absorbed by the human gastrointestinal tract, is claimed by the '506, '161, and '382 patents, however, none of the three prior art patents mention the use of piperine for enhancing the bioavailability of curcumin to retard the onset of symptoms of Alzheimer's disease in humans as claimed by the applicant's current patent application.

Galantamine, a natural plant extract derived from the daffodil, snowdrop, and the spider lily, is an acetylcholinesterase inhibitor. Acetylcholinesterase is an enzyme that breaks down acetylcholine in the synaptic cleft between nerve cells. Acetylcholine is involved in memory and learning processes. Research has shown that the level of acetylcholine present in the nervous system of Alzheimer's patients is abnormally low. Galantamine increases the level of acetylcholine present in the brain by inhibiting the activity of acetylcholinesterase. In addition to being a useful therapeutic agent in the treatment of Alzheimer's disease, galantamine may also be useful for treating mild cognitive impairment, an age-related condition often diagnosed as a precursor condition and risk factor for developing Alzheimer's. Galantamine is also effective in treating Alzheimer's disease because it works to modulate nicotinic receptors on brain cells, which respond to acetylcholine, thereby preserving the number and functional integrity of nicotinic receptors in the brain. In Alzheimer's patients, the number and functional integrity of nicotinic receptors is diminished resulting in fewer receptors for acetylcholine. The benefits of treating Alzheimer's with galantamine are not affected by previous treatments using other acetylcholinesterase inhibitors. Thus, galantamine may work to effectively halt the progression of Alzheimer's disease and also allows a patient to regain some memory and cognitive functions as well as being able to perform some simple tasks of daily living. None of the three prior art patents mention the use of piperine for enhancing the bioavailability of galantamine to retard the onset of symptoms of Alzheimer's disease in humans as claimed by the applicant's current patent application.

Huperzine A, an alkaloid plant extract from the club moss Huperzia serrata, is a nootropic agent that also strongly inhibits the activity of acetylcholinesterase. As huperzine A inhibits the breakdown of acetylcholine by acetylcholinesterase, more acetylcholine becomes available to stimulate neurons. Huperzine A provides a long-lasting, potent means for inhibiting the enzymatic activity of acetylcholinesterase, thereby increasing the amount of acetylcholine present within the nervous system. The prior art does not describe the use of piperine for enhancing the bioavailability of huperzine A to retard the onset of symptoms of Alzheimer's disease in humans as claimed by the applicant's current patent application.

Oleic acid increases the absorptivity of the intestines so that food and nutrients can be fully absorbed into the body. In this way, oleic acid aids the body in digesting and processing substances that are difficult to digest. Bile (phosphatidylcholine) is the body's principle source of oleic acid in the small intestine, however only small amounts are produced. Oleanolic acid and ursolic acid share similar properties with oleic acid and also enhance the effects of curcumin in the body. The prior art, including the United States patents discussed above, does not describe the use of piperine for enhancing the bioavailability of oleic acid to retard the onset of symptoms of Alzheimer's disease in humans as claimed by the applicant's current patent application.

Pyritinol is a vitamin B6 derivative that improves glucose uptake within the brain, has antioxidant abilities, and enhances the immune system by increasing neutrophil activity. The Food and Drug Administration approved pyritinol for use to improve memory, concentration, and vigilance. Once again, the prior art does not describe the use of piperine for enhancing the bioavailability of pyritinol to retard the onset of symptoms of Alzheimer's disease in humans as claimed by the applicant's current patent application.

Vinpocetine is another drug that has shown memory-enhancing properties in humans. Vinpocetine is believed to enhance blood flow in the brain, safeguard brain cells against damage, and inhibit the activity of a substance known as phosphodiesterase, all of which would retard the chances of developing symptoms of Alzheimer's disease.

Vitamin B5, or pantothenic acid, is used by the human body along with choline to form acetylcholine. Thus, as important precursors to the formation of acetylcholine, which is often present in reduced levels in Alzheimer's patients, choline and vitamin B5 are necessary nutritional supplements for preventing the onset of symptoms associated with neurodegenerative disorders, such as Alzheimer's.

Gamma tocopherol, an analog of vitamin E, has been proven to act as a strong antioxidant useful in the prevention of the symptoms of Alzheimer's disease in humans. Sesame lignans, preferably in the form of sesamolin, enhances the bioavailability of gamma tocopherol at the cellular level, thereby increasing the effectiveness of gamma tocopherol in combating the effects of the symptoms of Alzheimer's disease.

U.S. Pat. No. 6,572,899, issued to Gorsek on Jun. 3, 2003, describes a composition of orally ingestible nutrients for treating memory loss, dementia, and Alzheimer's disease. The '899 patent does not describe the use of curcumin and piperine to delay the onset of symptoms of Alzheimer's disease as does the applicant's application.

U.S. Pat. No. 6,486,194, issued to Ducharme et al., on Nov. 26, 2002, describes the use of enzyme inhibitors to disrupt the activity of cyclooxygenase to treat neurodegenerative diseases, including Alzheimer's disease. Although the '194 patent claims the oral administration of an enzyme inhibitor, the particular enzyme inhibited in that patent is not acetylcholinesterase, nor does the '194 invention describe the use of curcumin or piperine to retard the symptoms of Alzheimer's disease.

U.S. Pat. No. 6,646,013, issued to Barker et al., on Nov. 11, 2003, describes a composition including multiple nutrients for reducing the risk of colorectal cancer in mammals. The '013 patent claims the use of curcumin as one of the cancer-preventing nutrients, however, the '013 does not describe the use of curcumin for preventing the onset of the symptoms of Alzheimer's disease in humans.

U.S. Pat. No. 6,133,306, issued to Beal on Oct. 17, 2000, describes a method of inhibiting neurodegenerative diseases, including Alzheimer's disease, by administering nitroindazole to a patient to inhibit a neuronal oxide synthase. The '306 patent does not describe the use of curcumin or piperine to delay the onset of the symptoms of Alzheimer's disease in humans.

SUMMARY

The invention is for compositions and methods for using said compositions as a dietary supplement to retard the onset of the symptoms of Alzheimer's disease in humans. The composition can include a mixture of curcumin, piperine, oleic acid, oleanolic acid, ursolic acid, galantamine, huperzine A, choline, and vitamin B5. The composition may also include gamma tocopherol, sesame lignans preferably in the form of sesamolin, vinpocetine, and/or pyritinol. Said composition can be produced as a dietary supplement for human ingestion in any orally administrable form including, but not limited to, a caplet, capsule, tablet, jelly, serum, or drink. Piperine, a botanical pepper extract derived from the fruits of *Piper nigrum* (black pepper) and *Piper longum* (long pepper), increases the bioavailability of curcumin in humans by increasing the absorption of curcumin from the gastrointestinal tract into the bloodstream.

The composition can contain each ingredient in the following ranges: about 2 to about 100 mg curcumin, about 2 to about 20 mg piperine, about 20 to about 100 mg oleic acid, about 20 to about 100 mg oleanolic acid, about 20 to about 100 mg ursolic acid, about 5 to about 200 mg galantamine, about 25 to about 250 μg huperzine A, about 5 to about 150 mg choline, and about 20 to about 200 mg vitamin B5. Gamma tocopherol, an optional ingredient, is included in the range of about 150 to about 250 mg, and sesamolin, another optional ingredient, is included in the composition at about 10 to about 40 mg. If desired, vinpocetine, which is an optional ingredient of the mixture, can be included at about 5 to about 150 mg, and pyritinol, also an optional ingredient in the composition, may be included in an amount ranging from about 20 to about 200 mg.

An object of this invention is to provide a composition, ingestible as a dietary supplement, for delaying the onset and progression of symptoms of Alzheimer's disease in humans.

Another object of this invention is to provide a composition for retarding the onset and progression of symptoms of Alzheimer's disease in humans that contains curcumin.

Still another object of this invention is to increase the bioavailability of curcumin and other nutrients ingested by including piperine in a composition for retarding the onset and progression of symptoms of Alzheimer's disease in humans.

Yet another object of this invention is to provide an additional source of choline to the human body for use in forming acetylcholine, thereby enhancing the functionality of nerves in the brain, which use acetylcholine for neural transmissions.

A further object of this invention is to provide a composition for retarding the onset and progression of symptoms of Alzheimer's disease in humans that will prevent the aggregation of and dissolve β-amyloid protein fragments in the brain.

Another object of this invention is to provide a method for retarding the onset and progression of the symptoms of Alzheimer's disease in humans using the composition described herein as an ingestible dietary supplement taken orally in a beneficial regimen to be clinically determined.

In accordance with these and other objects which will become apparent hereinafter, the instant invention will now be described with particular reference to the accompanying drawings.

Accordingly, the invention features a composition used as a dietary supplement for orally administering to human patients who have manifested the symptoms of an early stage of Alzheimer's disease as diagnosed by their physician. The composition can include effective amounts of curcumin, piperine, oleic acid, oleanolic acid, galantamine, huperzine A, choline; and vitamin B5.

In another aspect, the invention can feature the composition further including one of phytic acid, piracetam, aniracetam, and indium.

In another aspect, the invention can feature the composition further including two of phytic acid, piracetam, aniracetam, and indium.

In another aspect, the invention can feature the composition further including three of phytic acid, piracetam, aniracetam, and indium.

In another aspect, the invention can feature the composition further including phytic acid, piracetam, aniracetam, and indium.

In another aspect, the invention can feature the composition further including ursolic acid.

In another aspect, the invention can feature the composition further including vinpocetine.

In another aspect, the invention can feature the composition further including gamma tocopherol.

In another aspect, the invention can feature the composition further including sesame lignans.

In another aspect, the invention can feature the sesame lignans being sesamolin and/or pyritinol.

The invention also features a dietary supplement for oral ingestion by a human to delay the onset of symptoms of Alzheimer's disease. The dietary supplement can include curcumin, piperine, oleic acid, oleanolic acid, galantamine, huperzine A, choline; and vitamin B5.

In another aspect, the invention can feature the composition further including at least one ingredient selected from the group of: phytic acid, piracetam, aniracetam, and indium.

A method of the invention can be used to delay the onset of symptoms of Alzheimer's disease in a human by administering to a subject in need thereof a dietary supplement composition that includes effective amounts of curcumin, piperine, oleic acid, oleanolic acid, galantamine, huperzine A, choline; and vitamin B5.

Another method of the invention can feature the composition further including vinpocetine, gamma tocopherol, and/or sesame lignans, wherein the sesame lignans are preferably in the form of sesamolin, and/or pyritinol.

Another method of the invention can feature the composition further including one of phytic acid, piracetam, aniracetam, and indium.

Another method of the invention can feature the composition further including two of phytic acid, piracetam, aniracetam, and indium.

Another method of the invention can feature the composition further including three of phytic acid, piracetam, aniracetam, and indium.

Another method of the invention can feature the composition further including phytic acid, piracetam, aniracetam, and indium.

Another method of the invention can feature the composition being produced in any orally ingestible form including, but not limited to, a caplet, a capsule, a tablet, a jelly, a serum, or a drink.

Another method of the invention can feature the composition being administered to the human daily.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The invention provides a composition for use as an orally-administered dietary supplement to delay the onset of symptoms of Alzheimer's disease in humans. The composition can include a mixture of curcumin for delaying the onset and progress of Alzheimer's disease symptomology in humans and piperine, a botanical pepper extract, for increasing the bioavailablity of curcumin in the bloodstream when said curcumin is orally administered to a patient. In exemplary embodiments, the composition also can include oleic acid, oleanolic acid, ursolic acid, galantamine, huperzine A, choline, and vitamin B5. The composition may further include vinpocetine, pyritinol, gamma tocopherol, and/or sesame lignans, preferably in the form of sesamolin. The composition can be produced as a dietary supplement for human ingestion in any orally administrable form including, but not limited to, a caplet, capsule, tablet, jelly, serum, or drink. Piperine, a botanical pepper extract, is derived from the fruits of plants in the Piperaceae family, and preferably from the fruits of *Piper nigrum* and *Piper longum*. In exemplary embodiments, the piperine used in the composition is derived from the fruits of Piper nigrum, i.e. black pepper. The purpose of including piperine is to increase the bioavailability of curcumin and other substances in humans by increasing the absorption of curcumin and other nutrients from the gastrointestinal tract.

EXAMPLE 1

Bioavailability Studies: Curcumin and Piperine

In this study, the bioavailability of curcumin was evaluated, with said curcumin being orally administered to animals, and subsequently, to normal healthy human volunteers along with a source of piperine (Bioperine® was the source of piperine used in this study). When taken orally only traces of curcumin appeared in the blood, whereas most of the oral dose was excreted though the feces. In both the preclinical studies performed on rats and in the clinical studies using normal healthy volunteers, piperine enhanced the bioavailability of curcumin.

EXAMPLE 2

Proposed Clinical Trial of the Effectiveness of the Composition in Treating the Symptoms of Alzheimer's Disease To test the effectiveness of the composition in delaying the onset of the symptoms of Alzheimer's disease, a dietary supplement preparation is administered orally to patients who have manifested the symptoms of an early stage of Alzheimer's disease, as diagnosed by their physician and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, at 6 weeks, and at 3 months during the clinical trial. The tests are performed by neuropsychologists who are not aware of the patients' treatment regimen.

In this double blind study, patients are randomly assigned to the test composition or placebo at the beginning of the study. The test composition and placebo are administered orally one or two times per day. The test patients are evaluated for a period of five years to determine the effectiveness of treatment using the composition as compared to the control group individuals given a placebo. Scores are statistically compared between the test composition and the placebo for each of the three observational periods. Without treatment, the natural course of Alzheimer's disease results in significant deterioration of a patient's test scores during the course of the clinical trial. A patient treated with the composition is considered improved if the patient's scores remain the same or improve during the course of the clinical trial.

In exemplary embodiments, the composition contains the following ingredients in the following ranges and preferred ranges: Curcumin can be included in the composition in a range of about 2 to about 100 mg. For example, each daily dosage of the composition can include curcumin in the amount of about 0.5, 0.75, 0.9, 1, 1.05, 1.5, 1.75, 1.9, 1.95, 1.99, 2, 2.05, 2.09, 2.1, 2.5, 3, 4, 4.5, 4.9, 5, 5.1, 5.5, 5.9, 10, 25, 50, 75, 95, 98, 99, 99.1, 99.5, 99.9, 100, 100.1, 100.5, 100.9, 101, 102, 105, or 110 mg. In a more preferred embodiment, curcumin can be included in the composition in a range of about 10 to about 40 mg.

Piperine can be included in the composition in a range of about 2 to about 20 mg. For example, each daily dosage of the composition can include piperine in the amount of about 0.5, 0.75, 0.9, 1, 1.05, 1.5, 1.75, 1.9, 1.95, 1.99, 2, 2.05, 2.09, 2.1, 2.5, 3, 4, 4.5, 4.9, 5, 5.1, 5.5, 5.9, 6, 8, 9, 10, 11, 15, 17, 18, 19, 19.1, 19.5, 19.9, 20, 20.1, 20.5, 20.9, 21, 22, or 25 mg. In a more preferred embodiment, piperine can be included in the composition in a range of about 5 to about 10 mg.

Oleic acid can be included in the composition in a range of about 20 to about 100 mg. For example, each daily dosage of the composition can include oleic acid in the amount of about 15, 17, 18, 19, 19.1, 19.5, 19.9, 20, 20.1, 20.5, 20.9, 21, 22, 25, 10, 25, 30, 35, 50, 70, 75, 90, 95, 98, 99, 99.1, 99.5, 99.9, 100, 100.1, 100.5, 100.9, 101, 102, 105, or 110 mg. In a more preferred embodiment, oleic acid can be included in the composition in an amount of about 40 mg.

Oleanolic acid can be included in the composition in a range of about 20 to about 100 mg. For example, each daily dosage of the composition can include oleanolic acid in the amount of about 15, 17, 18, 19, 19.1, 19.5, 19.9, 20, 20.1, 20.5, 20.9, 21, 22, 25, 10, 25, 30, 35, 50, 70, 75, 90, 95, 98, 99, 99.1, 99.5, 99.9, 100, 100.1, 100.5, 100.9, 101, 102, 105, or 110 mg. In a more preferred embodiment, oleanolic acid can be included in the composition in an amount of about 40 mg.

Ursolic acid can be included in the composition in a range of about 20 to about 100 mg. For example, each daily dosage of the composition can include ursolic acid in the amount of about 15, 17, 18, 19, 19.1, 19.5, 19.9, 20, 20.1, 20.5, 20.9, 21, 22, 25, 10, 25, 30, 35, 50, 70, 75, 90, 95, 98, 99, 99.1, 99.5, 99.9, 100, 100.1, 100.5, 100.9, 101, 102, 105, or 110 mg. In a more preferred embodiment, ursolic acid can be included in the composition in an amount of about 40 mg.

Galantamine can be included in the composition in a range of about 5 to about 200 mg. For example, each daily dosage of the composition can include galantamine in the amount of about 1, 2.5, 3, 4, 4.5, 4.9, 5, 5.1, 5.5, 5.9, 10, 25, 50, 75, 100, 110, 120, 125, 130, 135, 140, 150, 160, 170, 175, 180, 190, 195, 198, 199, 199.1, 199.5, 199.9, 200, 200.1, 200.5, 200.9, 201, 202, 205, or 210 mg. In a more preferred embodiment, galantamine can be included in the composition in a range of about 16 to about 24 mg.

Huperzine A can be included in the composition in a range of about 25 to about 250 µg. For example, each daily dosage of the composition can include huperzine A in the amount of about 20, 21, 22, 22.5, 23, 24, 24.1, 24.5, 24.9, 25, 25.1, 25.5, 25.9, 26, 30, 35, 50, 70, 75, 90, 100, 110, 120, 125, 130, 135, 140, 150, 160, 170, 175, 180, 190, 200, 210, 220, 230, 240, 245, 249, 249.1, 249.5, 249.9, 250, 250.1, 250.5, 250.9, 251, 252, 255, or 260 µg. In a more preferred embodiment, huperzine A can be included in the composition in a range of about 50 to about 100 µg.

In other embodiments, the composition can include one or more of the following optional ingredients in the following ranges and preferred ranges:

Choline can be included in the composition in a range of about 5 to about 150 mg. For example, each daily dosage of the composition can include choline in the amount of about 1, 2.5, 3, 4, 4.5, 4.9, 5, 5.1, 5.5, 5.9, 10, 25, 30, 50, 60, 75, 80, 100, 110, 120, 125, 130, 135, 140, 145, 148, 149, 149.1, 149.5, 149.9, 150, 150.1, 150.5, 150.9, 151, 152, 155, 159, or 160 mg. In a more preferred embodiment, choline can be included in the composition in a range of about 20 to about 50 mg.

Vitamin B5, or pantothenic acid, can be included in the composition in a range of about 20 to about 200 mg. For example, each daily dosage of the composition can include vitamin B5 in the amount of about 15, 17, 18, 19, 19.1, 19.5, 19.9, 20, 20.1, 20.5, 20.9, 21, 22, 25, 10, 25, 30, 35, 50, 70, 75, 90, 100, 110, 120, 125, 130, 135, 140, 150, 160, 170, 175, 180, 190, 195, 198, 199, 199.1, 199.5, 199.9, 200, 200.1, 200.5, 200.9, 201, 202, 205, or 210 mg. In a more preferred embodiment, vitamin B5 can be included in the composition in a range of about 50 to about 100 mg.

Gamma tocopherol, an optional ingredient, can be included in the composition in a range of about 150 to about 250 mg. For example, each daily dosage of the composition can include gamma tocopherol in the amount of about 135, 140, 145, 148, 149, 149.1, 149.5, 149.9, 150, 150.1, 150.5, 150.9, 151, 152, 155, 159, 160, 165, 170, 175, 180, 185, 190, 200, 210, 220, 230, 240, 245, 249, 249.1, 249.5, 249.9, 250, 250.1, 250.5, 250.9, 251, 252, 255, or 260 mg. In a more preferred embodiment, gamma tocopherol can be included in the composition in an amount of about 200 mg.

Sesame lignans, preferably in the form of sesamolin and also an optional ingredient, can be included in the composition in a range of about 10 to about 40 mg. For example, each daily dosage of the composition can include sesame lignans in the amount of about 6, 7, 7.5, 8, 9, 9.1, 9.5, 9.9, 10, 10.1, 10.5, 10.9, 11, 12.5, 13, 15, 20, 25, 30, 35, 37, 37.5, 38, 39, 39.5, 39.9, 40, 40.1, 40.5, 40.9, 41, 42, 42.5, 43, 44, or 45 mg. In a more preferred embodiment, sesame lignans can be included in the composition in an amount of about 20 mg.

If desired, vinpocetine, which is an optional ingredient of the mixture, can be included in the composition in a range of about 5 to about 150 mg. For example, each daily dosage of the composition can include vinpocetine in the amount of about 1, 2.5, 3, 4, 4.5, 4.9, 5, 5.1, 5.5, 5.9, 10, 25, 30, 50, 60, 75, 80, 100, 110, 120, 125, 130, 135, 140, 145, 148, 149, 149.1, 149.5, 149.9, 150, 150.1, 150.5, 150.9, 151, 152, 155, 159, or 160 mg. In a more preferred embodiment, vinpocetine can be included in the composition in a range of about 20 to about 50 mg.

Pyritinol, also an optional ingredient in the composition, can be included in an amount ranging from about 20 to about 200 mg. For example, each daily dosage of the composition can include pyritinol in the amount of about 15, 17, 18, 19, 19.1, 19.5, 19.9, 20, 20.1, 20.5, 20.9, 21, 22, 25, 10, 25, 30, 35, 50, 70, 75, 90, 100, 110, 120, 125, 130, 135, 140, 150, 160, 170, 175, 180, 190, 195, 198, 199, 199.1, 199.5, 199.9, 200, 200.1, 200.5, 200.9, 201, 202, 205, or 210 mg. In a more preferred embodiment, pyritinol can be included in the composition in an amount of about 100 mg.

In other embodiments, the composition can include one or more of phytic acid, piracetam, aniracetam, and indium. In various embodiments of the compositions, one, two, three, or all of these compounds may be included in different combinations. For example, in one embodiment, the composition could include only phytic acid. In another embodiment, the composition could include both piracetam and aniracetam. In still another embodiment, the composition could include phytic acid, piracetam, and indium. In yet another embodiment, the composition could include all four of these ingredients. At least one of phytic acid, piracetam, aniracetam, and indium can be included in the composition in combination with any of the foregoing ingredients described herein.

As an ingredient of the dietary supplement composition, phytic acid provides complete protection against amyloid precursor protein-C-terminal fragment-induced cytotoxicity by attenuating levels of increased intracellular calcium, hydrogen peroxide, superoxide, and β-amyloid oligomers. Phytic acid also moderately up-regulates the expression of autophagy (beclin-1) protein. Each daily dosage of the composition can include about 3 to about 6 grams of phytic acid. For example, each daily dosage of the composition can include phytic acid in the amount of about 2, 2.1, 2.2, 2.25, 2.5, 2.6, 2.75, 2.8, 2.9, 2.95, 2.99, 3, 3.05, 3.1, 3.25, 3.3, 3.5, 4, 4.5, 5, 5.5, 5.7, 5.75, 5.8, 5.9, 5.95, 5.99, 6, 6.01, 6.05, 6.1, 6.25, 6.5, 6.75, or 7 g. In another embodiment, each daily dosage of the composition can include phytic acid in a range of about 5 to about 500 mg/kg of bodyweight. For example, each daily dosage of the composition can include indium in the amount of about 1, 2.5, 3, 4, 4.5, 4.9, 5, 5.1, 5.5, 5.9, 10, 25, 35, 50, 75, 100, 150, 200, 225, 250, 275, 300, 350, 400, 410, 425, 450, 475, 480, 490, 495, 498, 499, 499.1, 499.5, 499.9, 500, 500.1, 500.5, 500.9, 501, 502, 505, 510, 520, 525, 530, or 550 mg/kg of bodyweight. In a more preferred embodiment, the composition can include phytic acid in a range of about 25 to about 250 mg/kg of bodyweight. In a most preferred embodiment, the composition can include phytic acid in an amount of about 35 mg/kg of bodyweight.

As an ingredient of the dietary supplement composition, piracetam activates the PPAR-γ receptor and reduces amyloid plaques. In some embodiments, each daily dosage of the composition can include about 1 to about 4 grams of piracetam. For example, each daily dosage of the composition can include piracetam in the amount of about 0.1, 0.2, 0.25, 0.5, 0.6, 0.75, 0.8, 0.9, 0.95, 0.99, 1, 1.05, 1.1, 1.25, 1.3, 1.5, 2, 2.5, 3, 3.5, 3.7, 3.75, 3.8, 3.9, 3.95, 3.99, 4, 4.01, 4.05, 4.1, 4.25, 4.5, 4.75, or 5 g. In another embodiment, each daily dosage of the composition can include piracetam in a range of about 200 to about 400 mg/kg of bodyweight. For example, each daily dosage of the composition can include piracetam in the amount of about 190, 195, 199, 199.5, 199.9, 200, 200.1, 200.5, 200.9, 201, 202, 205, 210, 250, 275, 290, 300, 325, 350, 375, 395, 398, 399, 399.1, 399.5, 399.9, 400, 400.1, 400.5, 400.9, 401, 402, 405, or 410 mg/kg of bodyweight. In a more preferred embodiment, the composition can include piracetam in a range of about 250 to about 350 mg/kg of bodyweight. In a most preferred embodiment, the composition can include piracetam in an amount of about 300 mg/kg of bodyweight.

As an ingredient of the dietary supplement composition, aniracetam is a fat-soluble variant of piracetam that activates the PPAR-γ receptor and reduces amyloid plaques. In some embodiments, each daily dosage of the composition can include about 1 to about 4 grams of aniracetam. For example, each daily dosage of the composition can include aniracetam in the amount of about 0.1, 0.2, 0.25, 0.5, 0.6, 0.75, 0.8, 0.9, 0.95, 0.99, 1, 1.05, 1.1, 1.25, 1.3, 1.5, 2, 2.5, 3, 3.5, 3.7, 3.75, 3.8, 3.9, 3.95, 3.99, 4, 4.01, 4.05, 4.1, 4.25, 4.5, 4.75, or 5 g. In another embodiment, each daily dosage of the composition can include aniracetam in a range of about 200 to about 400 mg/kg of bodyweight. For example, each daily dosage of the composition can include aniracetam in the amount of about 190, 195, 199, 199.5, 199.9, 200, 200.1, 200.5, 200.9, 201, 202, 205, 210, 250, 275, 290, 300, 325, 350, 375, 395, 398, 399, 399.1, 399.5, 399.9, 400, 400.1, 400.5, 400.9, 401, 402, 405, or 410 mg/kg of bodyweight. In a more preferred embodiment, the composition can include aniracetam in a range of about 250 to about 350 mg/kg of bodyweight. In a most preferred embodiment, the composition can include aniracetam in an amount of about 300 mg/kg of bodyweight.

As an ingredient of the dietary supplement composition, indium helps to restore hormone levels that normally decrease with age. Each daily dosage of the composition can include about 5 to about 100 mg of indium. For example, each daily dosage of the composition can include indium in the amount of about 1, 2.5, 3, 4, 4.5, 4.9, 5, 5.1, 5.5, 5.9, 10, 25, 50, 75, 95, 98, 99, 99.1, 99.5, 99.9, 100, 100.1, 100.5, 100.9, 101, 102, 105, or 110 mg. In a more preferred embodiment, each daily dosage of the composition can include indium in a range of about 10 to about 50 mg. In a most preferred embodiment, each daily dosage of the composition can include aniracetam in an amount of about 20 mg.

This invention also relates to a method for delaying the onset of symptoms of Alzheimer's disease in humans using the above-described composition as an ingestible dietary supplement. Preferably, the dietary supplement containing the composition is taken once or twice daily by a user. In this method, said composition may be produced and ingested in any orally administrable form including, but not limited to, a caplet, capsule, tablet, jelly, serum, or drink. The composition and method may also be used to delay the onset of symptoms of other neurodegenerative diseases, similar to Alzheimer's disease, that affect aging humans, including, but not limited to, Parkinson's disease.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition used as a dietary supplement for orally administering to human patients who have manifested the symptoms of an early stage of Alzheimer's disease as diagnosed by their physician, wherein the composition comprises effective amounts of:
   curcumin;
   piperine;
   oleic acid;
   oleanolic acid;
   galantamine;
   huperzine A;
   choline;
   vitamin B5;
   ursolic acid; and
   at least two of phytic acid, piracetam, aniracetam, and indium.

2. The composition of claim 1, comprising three of phytic acid, piracetam, aniracetam, and indium.

3. The composition of claim 1, comprising phytic acid, piracetam, aniracetam, and indium.

4. The composition according to claim 1, wherein the composition further comprises vinpocetine.

5. The composition according to claim 1, wherein the composition further comprises gamma tocopherol.

6. The composition according to claim 1, wherein the composition further comprises sesame lignans.

7. The composition according to claim 1, wherein the sesame lignans comprise sesamolin and/or pyritinol.

8. A dietary supplement for oral ingestion by a human to treat the symptoms of Alzheimer's disease, the dietary supplement comprising:
   curcumin;
   piperine;
   oleic acid;
   oleanolic acid;
   galantamine;
   huperzine A;
   choline;
   vitamin B5;
   ursolic acid; and
   at least two ingredients selected from the group consisting of phytic acid, piracetam, aniracetam, and indium.

9. A method for using a composition to treat the symptoms of Alzheimer's disease in a human, comprising administering to the human in need thereof a dietary supplement composition comprising effective amounts of:
   curcumin;
   piperine;
   oleic acid;
   oleanolic acid;
   galantamine;
   huperzine A;
   choline;
   vitamin B5;
   ursolic acid; and
   two of phytic acid, piracetam, aniracetam, and indium.

10. The method of claim 9, wherein the composition further comprises vinpocetine, gamma tocopherol, and/or sesame lignans, wherein the sesame lignans are preferably in the form of sesamolin, and/or pyritinol.

11. The method of claim 9, wherein the composition comprises three of phytic acid, piracetam, aniracetam, and indium.

12. The method of claim 9, wherein the composition comprises phytic acid, piracetam, aniracetam, and indium.

13. The method of claim 9, wherein the composition is produced in any orally ingestible form including, but not limited to, a caplet, a capsule, a tablet, a jelly, a serum, or a drink.

14. The method of claim 9, wherein the composition is administered to the human daily.

15. The dietary supplement of claim 8, further comprising vinpocetine, gamma tocopherol, and/or sesame lignans.

* * * * *